US00PP26437P2

(12) United States Plant Patent
Horvath

(10) Patent No.: US PP26,437 P2
(45) Date of Patent: Mar. 1, 2016

(54) ***GEUM* PLANT NAMED 'SEA BREEZE'**

(50) Latin Name: ***Geum* hybrid**
Varietal Denomination: Sea Breeze

(71) Applicant: Brent Horvath, Fontana, WI (US)

(72) Inventor: Brent Horvath, Fontana, WI (US)

( * ) Notice: Subject to any disclaimer, the term of this patent is extended or adjusted under 35 U.S.C. 154(b) by 236 days.

(21) Appl. No.: 13/987,452

(22) Filed: Jul. 26, 2013

(51) Int. Cl.
*A01H 5/02* (2006.01)

(52) U.S. Cl.
USPC ..... Plt./263.1

(58) Field of Classification Search
USPC ..... Plt./263.1
CPC ..... A01H 5/02; A01H 5/0216; A01H 5/00
See application file for complete search history.

*Primary Examiner* — Kent L Bell

(57) ABSTRACT

A new, distinct *Geum* plant as shown and described, characterized by spaced and folded petals on single deep orange flowers.

1 Drawing Sheet

Latin name: *Geum* hybrid.
Cultivar name: 'Sea Breeze'.

BACKGROUND OF THE INVENTION

The present invention relates to a new and distinct hybrid of *Geum* plant named 'Sea Breeze' characterized by spaced and folded petals on single deep orange flowers. The new *Geum* was discovered and developed as a seedling as part of an on going breeding and selecting program, in Hebron, Ill. in 2008. The selection of the new plant was due to its' uniquely spaced and folded petals on single deep orange flowers. The initial asexual propagation of the new plant was by division and took place at a nursery in Hebron, Ill. since 2009. Continued asexual propagation by division since that time has shown that the unique features of this new *Geum* plant are stable and reproduced true to type in successive generations.

SUMMARY OF THE INVENTION

In the following description, color references are made to The Royal Horticultural Society Colour Chart (2001). The new *Geum* plant named 'Sea Breeze' is characterized by spaced and folded petals on single deep orange flowers of RHS 34A.

The new *Geum* plant can be compared to 'Alabama Slammer' U.S. Plant Pat. No. 23,750, flower colors are orange RHS 44A blending into red RHS N34 while the new plant flower color is RHS 34 A. Also the size of *Geum* 'Alabama Slammer' plants are 35 cm while the new *Geum* plant reached 45 cm in maturity.

The new plant can also be compared to *Geum* 'Totally Tangerine' U.S. Plant Pat. No. 22,041, which is a sterile hybrid with lighter orange single flowers of 32 A, that fades to 169 C. Plants of *Geum* 'Totally Tangerine' also grow to 130 cm tall while the new plant only grows 45 cm tall at maturity.

DESCRIPTION OF PHOTOGRAPHS

Figure 1:
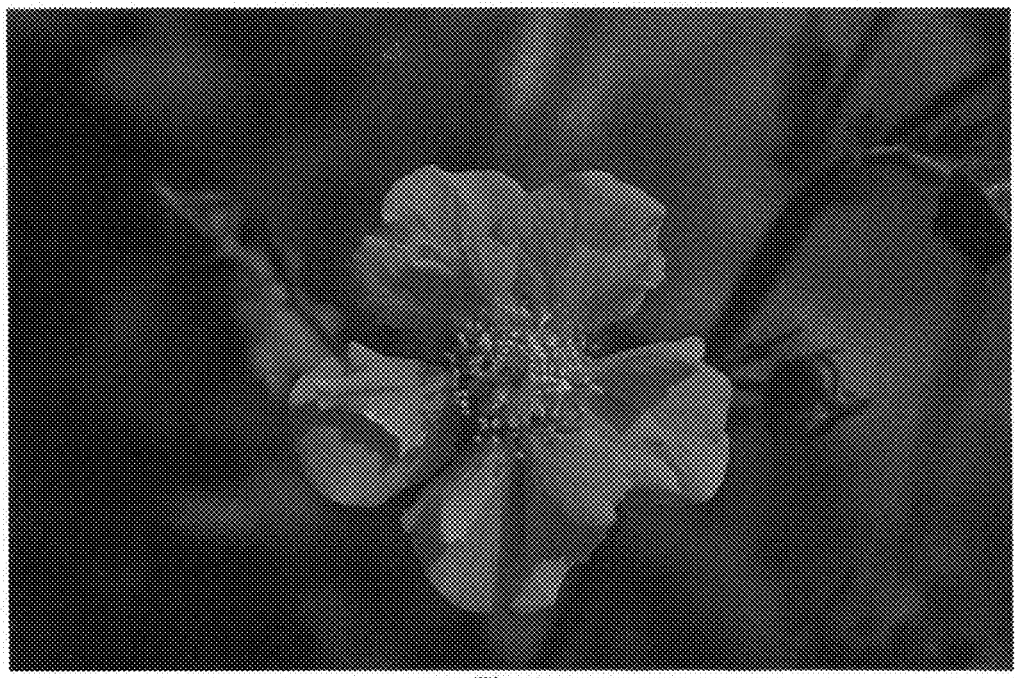
Figure 2:
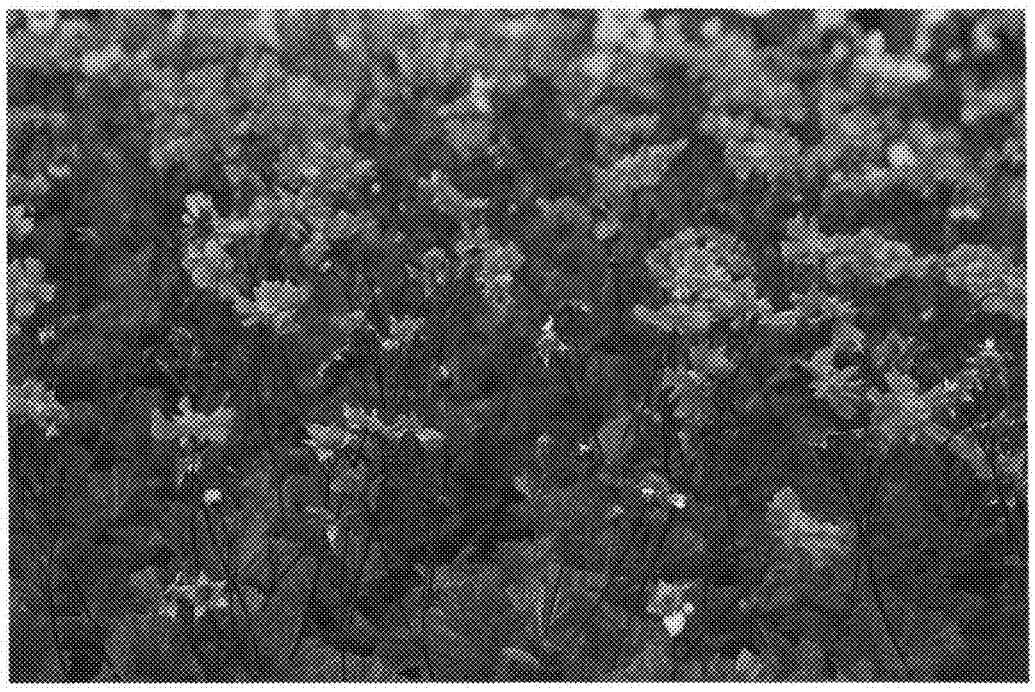

FIG. 1. Close up of the flower.
FIG. 2. Blooming plants in May.

DETAILED BOTANICAL DESCRIPTION

In the following description, color references are made to The Royal Horticultural Society Colour Chart (2001). Plants used for the description were grown in a 3 gallon container for two years at a nursery in Hebron, Ill. Measurements and numerical values represent averages of typical plants.

Botanical classification: *Geum* hybrid cultivar 'Sea Breeze'.

Parentage: Unknown.

Propagation: Vegetative division.

Plant description: Overall habit of the new *Geum* is basal clumps, upright burgundy flower stems topped by single deep orange flowers of RHS 34 A.

- *Plant type.*—Herbaceous perennial.
- *Plant height.*—45 cm.
- *Plant width.*—50 cm.
- *Stem.*—Diameter: 3 mm.
- *Stem or basal branches.*—Number of basal branches per plant: 25, length up to 45 cm, with the internode between basal foliage and first leaflet length being 12 cm and the second internode between the first leaflet and the second leaflet length being 6 cm and the third internode between the second and third leaflet length being 8 cm and the fourth internode between the third and fourth leaflet length being 4 cm.
- *Stem coloration.*—Close to 145A, to the coloration of the top of the stem is N77A.

Foliage description:

- *Type.*—Herbaceous.
- *Arrangement.*—Basal alternate with typically two or three lateral leaflets per stem.
- *Petiole.*—Up to 20 cm long, with a diameter of 3 mm, color close to 145 A.
- *Terminal compound leaf length.*—Up to 30 cm.
- *Terminal compound leaf width.*—12 cm.
- *Terminal leaflet length.*—Typically 3-4 cm.
- *Terminal leaflet width.*—Typically 2-3 cm.
- *Terminal leaflet shape.*—Obovate with incised margins.
- *Terminal and lateral leaf apex.*—Acute.
- *Terminal and lateral leaf base.*—Cuneate.
- *Terminal and lateral leaf margin.*—Incised.
- *Texture.*—Terminal and lateral leaf, upper and lower surfaces: pubescent.
- *Venation pattern.*—Terminal and lateral leaf, upper and lower surfaces: pinnate.

*Venation color.*—Terminal and lateral leaf, upper surface is color 148 A and lower surface color is 148 B.
*Lateral leaflet number.*—2 or 3 per stem.
*Lateral leaflet length.*—3 cm.
*Lateral leaflet width.*—Up to 2 cm.
*Lateral leaflet shape.*—Obovate.
*Adaxial leaf description.*—Color is 148 A.
*Abaxial leaf description.*—Color 148 B.

Flower description:

*Flower type.*—Corymb.
*Flower color.*—34A on top and 31 C on the bottom.
*Flower size.*—Diameter: 50 mm across, depth 20 mm.
*Flower number.*—4-5 per stem, 90-135 per plant.
*Number flowering stems.*—20-30.
*Bloom period and duration.*—Beginning the first week of May into the first week of June in Hebron, Ill.
*Flower longevity and duration on the plant.*—Approximately 3 weeks.
*Flower longevity and duration cut.*—Approximately one week.
*Individual flower duration.*—Approximately 1 to 2 weeks with petals eventually drying to a tan color.
*Scent.*—None.
*Petal count.*—10.
*Petal shape.*—Spatulate.
*Petal arrangement.*—Rotate, overlapping.
*Petal diameter or width.*—20 mm across and petal length — 18 mm long.
*Petal apex.*—Retuse, base: attenuate, margin: entire.
*Petal texture.*—Upper and lower surfaces: smooth, glabrous.
*Petal color.*—Upper surface is color 34 A.
*Petal color.*—Lower surface color is close to 31 C.
*Overall corymb size.*—Diameter and height — 18 cm across, 16 cm long.
*Flower buds.*—Diameter: 16 mm across, depth: 12 mm, shape: ovoid, surface: slightly pubescent and color between 59A and 59B.
*Sepal size.*—Length: up to 18 mm, diameter: 8 mm at base coming to a point.
*Sepal quantity.*—6.
*Sepal shape.*—Lanceolate, apex: acute, base: cuneate, margin: entire.
*Sepal texture.*—Upper and lower surfaces: Pubescent.
*Sepal color.*—Adaxial color is brown to red-purple. Abaxial color 59 A.
*Peduncle color.*—Purple N 77 A.
*Peduncle size.*—Length: 30 mm, diameter: 3 mm.
*Pedicel size.*—Length: 12 cm, diameter: 1-2 mm and color N77 A.
*Reproductive organs.*—Stamen — quantity over 100, length 1 cm.
*Anther.*—Quantity: over 100, length: 1 mm, diameter: close to 0.5 mm.
*Pollen.*—Typically present, color: 12A.
*Stigma.*—Number over 50, width less than 1 mm, general color is orange.
*Style.*—Number: over 50, length: 6 mm, general color is orange.
*Pistil.*—Number: over 50, length: 6+ mm.
*Ovaries.*—Number: over 50 per bloom average, color: is green.
*Fruit.*—Number: over 50 per bloom average, color: is brown, tear shaped, length — 9-10 mm, width — 2 mm.
*Hardiness.*—USDA zone 4 to 9.

Disease resistance: Resistance to diseases common to *Geum* has not been observed on plants grown under nursery conditions.

I claim:

1. A new, distinct *Geum* plant as illustrated and described, characterized by spaced and folded petals on single deep orange flowers.

* * * * *